(12) United States Patent
Allard

(10) Patent No.: US 8,469,914 B2
(45) Date of Patent: Jun. 25, 2013

(54) COMPRESSION DEVICE

(75) Inventor: Peter Allard, Helsingborg (SE)

(73) Assignee: Camp Scandinavia AB, Helsingborg (SE)

( * ) Notice: Subject to any disclaimer, the term of this patent is extended or adjusted under 35 U.S.C. 154(b) by 554 days.

(21) Appl. No.: 12/532,951

(22) PCT Filed: Mar. 18, 2008

(86) PCT No.: PCT/EP2008/053220
§ 371 (c)(1),
(2), (4) Date: Feb. 8, 2010

(87) PCT Pub. No.: WO2008/116791
PCT Pub. Date: Oct. 2, 2008

(65) Prior Publication Data
US 2010/0168636 A1 Jul. 1, 2010

(30) Foreign Application Priority Data
Mar. 28, 2007 (EP) .................................. 07105122

(51) Int. Cl.
*A61F 13/06* (2006.01)
(52) U.S. Cl.
USPC .......................................... 602/62

(58) Field of Classification Search
USPC .............................. 602/61–65, 78; 2/239, 409
See application file for complete search history.

(56) References Cited

U.S. PATENT DOCUMENTS

| 3,538,914 | A | * | 11/1970 | Myers | 24/306 |
| 3,902,503 | A | * | 9/1975 | Gaylord, Jr. | 450/135 |
| 5,385,036 | A | * | 1/1995 | Spillane et al. | 66/87 |
| 5,653,244 | A | * | 8/1997 | Shaw | 128/882 |
| 6,945,944 | B2 | * | 9/2005 | Kuiper et al. | 602/13 |
| 7,037,282 | B2 | | 5/2006 | Coleman | |
| 2003/0195449 | A1 | | 10/2003 | Coleman | |

FOREIGN PATENT DOCUMENTS

| EP | 1210924 A | 6/2002 |
| WO | 9516416 A | 6/1995 |
| WO | 03077791 A | 9/2003 |
| WO | 2006048619 A | 5/2006 |

* cited by examiner

*Primary Examiner* — Patricia Bianco
*Assistant Examiner* — Raymond E Harris
(74) *Attorney, Agent, or Firm* — Volpe and Koenig, P.C.

(57) ABSTRACT

The invention relates to a compression device and particularly a compression device provided with fastening means to provide an adjustability of the circumference enabling controllable compression of the device. In particular, present invention relates to a compression device or legging with fastening means comprising a tongue with multiple zip fasteners.

10 Claims, 5 Drawing Sheets

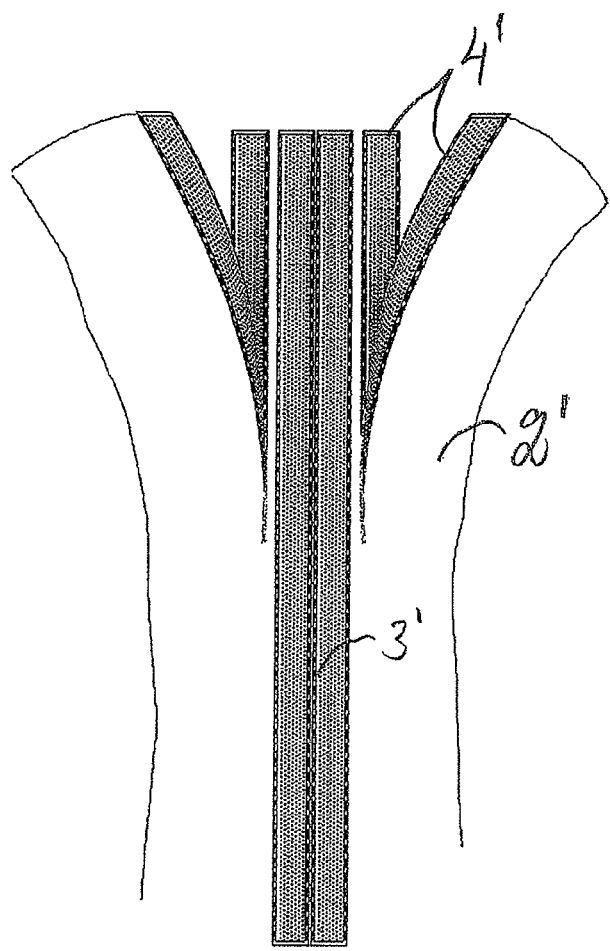
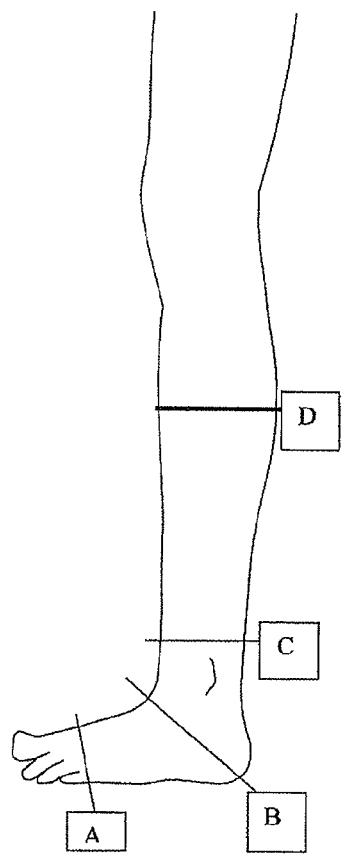
FIG 6    FIG 7
FIG 10

COMPRESSION DEVICE

FIELD OF INVENTION

The present invention relates to a compression device and particularly a compression device provided with fastening means to provide an adjustability of the circumference enabling controllable compression of the device. In particular, present invention relates to a compression device or legging with fastening means comprising a tongue with multiple zip fasteners.

BACKGROUND OF THE INVENTION

Generally, compression devices refer to appliances for medical treatment of body parts. The compression device is adapted to apply a controlled pressure in connection with various treatments. Typical examples are corsets, orthoses for arms and legs, such as leggings.

To improve foot wound healing, e.g. on patients having diabetes, it is known to provide compression around the lower leg, since this will increase the blood circulation through the wound.

It is not possible to use commercially available pressure stockings, since these have to be pulled over the foot, which can adversely affect the wound. It is therefore necessary to construct leggings, which can easily be taken on and off. Providing them with zip fasteners can take care of this need.

US 2003/0195449 and U.S. Pat. No. 7,037,282 show examples of medical support appliances provided with a single zip lock. The appliances have a fixed circumference and have to be custom made for each patient to provide optimal effect. Thus, there is a need for an off-the-shelf item with controllable compression that does not have to be tailored to each patient.

SUMMARY OF THE INVENTION

An object of the present invention is to provide a compression device in a number of sizes fitting the majority of the population with controllable compression.

A further object of the present invention is to provide such a compression legging.

The legging may be worn with or without and outer rigid shell together providing an orthosis.

The present invention provides a compression device for providing compression on a body part. The compression device comprises a main part for substantially covering a main portion of the body part, and a tongue attachable to the main part for completing the circumference around the body part, wherein the main part at each edge is provided with fastening means attachable to the tongue.

In one embodiment, the compression device comprises a legging for providing compression on a leg and foot, comprising a main part for substantially covering the sides of the leg and sides and plantar side of the foot, and a tongue attachable to the main part for completing the circumference of the leg and the foot.

Suitably, the main part at each edge is provided with one half of a fastening means, and the tongue is provided with a number of halves of the fastening means mating with the half provide on the main part.

The tongue may be provided with at least three halves.

The invention is defined in the appended claim 1, while embodiments are set forth in the dependent claims.

BRIEF DESCRIPTION OF THE DRAWINGS

The invention will be described in detail below with reference to the accompanying drawings, in which:

FIG. 6 is a front view of a tongue and main part according to a further embodiment of the invention, FIG. 7 is a side view of a leg with reference positions, FIG. 10 is a view of a legging inserted in a shell according to one embodiment of the invention.

DETAILED DESCRIPTION OF THE PREFERRED EMBODIMENTS

The invention generally relates to a medical support appliance in the form of compression devices, such as corsets, orthoses for arms and legs, such as leggings. The invention will be described with reference to a compression legging for treating foot wounds.

Several studies have shown that it is positive for patients suffering from ulcers and/or oedema to use compression stockings or other equipment giving the same effect. The reason is that the increased pressure stimulates the blood flow through the wound. The increased pressure (typically 15-20 mm Hg) around the leg can be achieved with a bandage, but this takes rather long time to apply and requires a skilled person.

It is not possible to use traditional pressure stockings, since these have to be pulled over the foot, which can adversely affect to wound and relocate dressings or the like on the foot. It is therefore necessary to have a product which can easily be taken on and off.

Orthoses comprising an inner legging, and an outer rigid shell have been used with good results. One problem is that the outer shell is cumbersome and often taken off for greater comfort. Some orthoses rely on the shell to provide adequate compression and thus the effect is lost. Thus, the legging should by itself be able to provide a large degree of compression. In a preferred embodiment, the legging essentially is manufactured of a stretchable material, suitably a 3D spacer material.

For best function the orthosis should also comprise an insole or other support member to distribute the pressure under the foot in a supportive and comfortable way.

Since it should be possible to take on and off the legging without pulling, it should be possible to open the legging. A zip lock can provide this function.

Embodiments of the present invention provide a legging that may be opened and fastened in an adjustable way providing controllable compression without needing an outer rigid shell.

Figure 1:
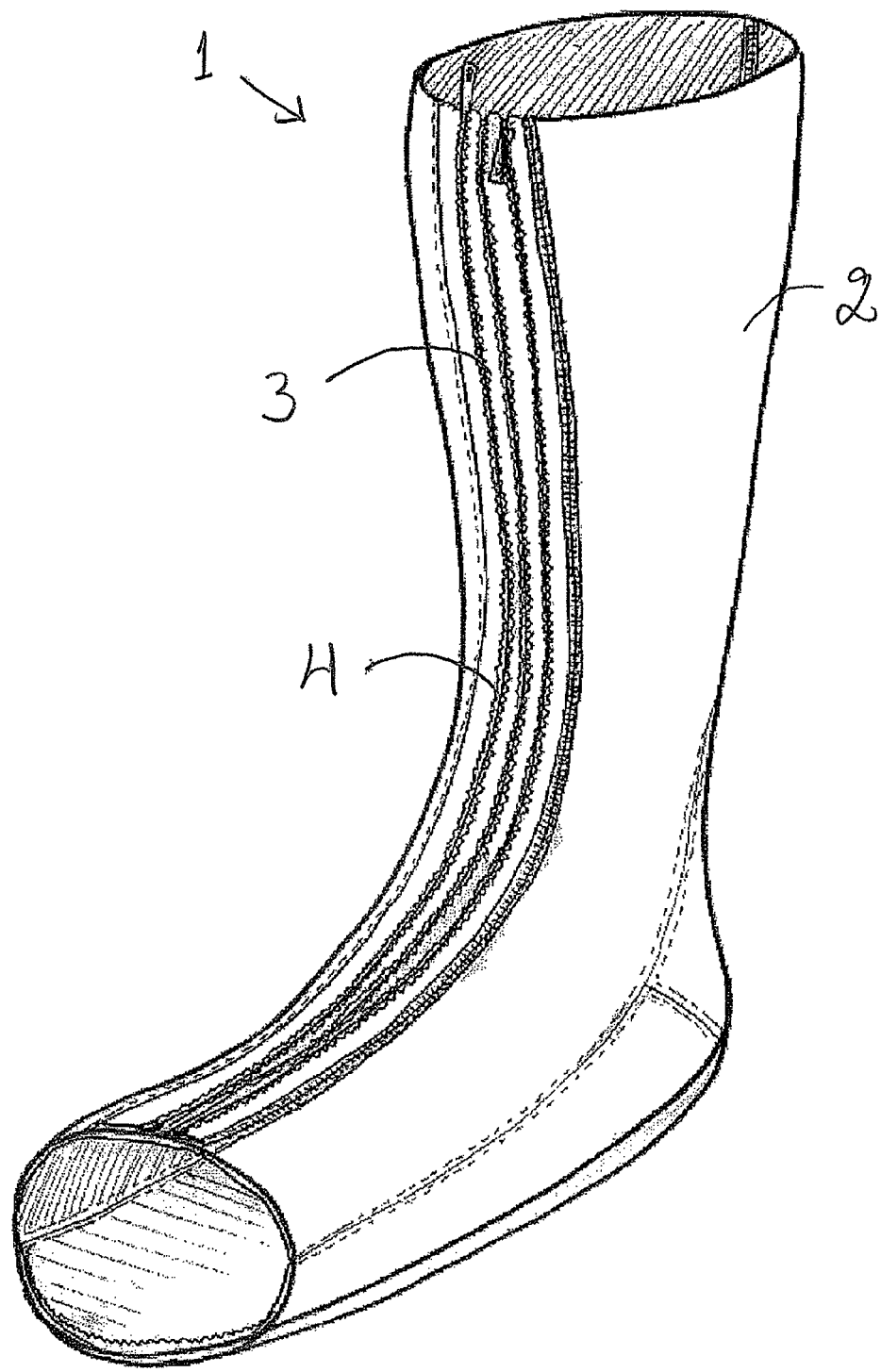
FIG. 1 is a perspective view of an embodiment of a compression device in the form of a legging according to the invention.

FIG. 1 shows a legging 1 according to the invention. The legging 1 comprises a main part 2 and a tongue 3. The main part 2 almost completely encircles the lower leg and foot of a patient. Particularly, it covers the sides of the lower leg and the sides and plantar side of the foot. The legging or compression device can also be designed to cover the whole leg or another body part. At the front, the main part 2 is attachable to the tongue 3 completing the circumference of the legging 1. For opening the legging 1 the whole tongue 3 is removed. The tongue 3 is fastened the main part 2 by means of a zip arrangement 4.

The same legging may be used for the left and right foot. The legging may be provided with a standard or individually adapted insole.

Figure 2:
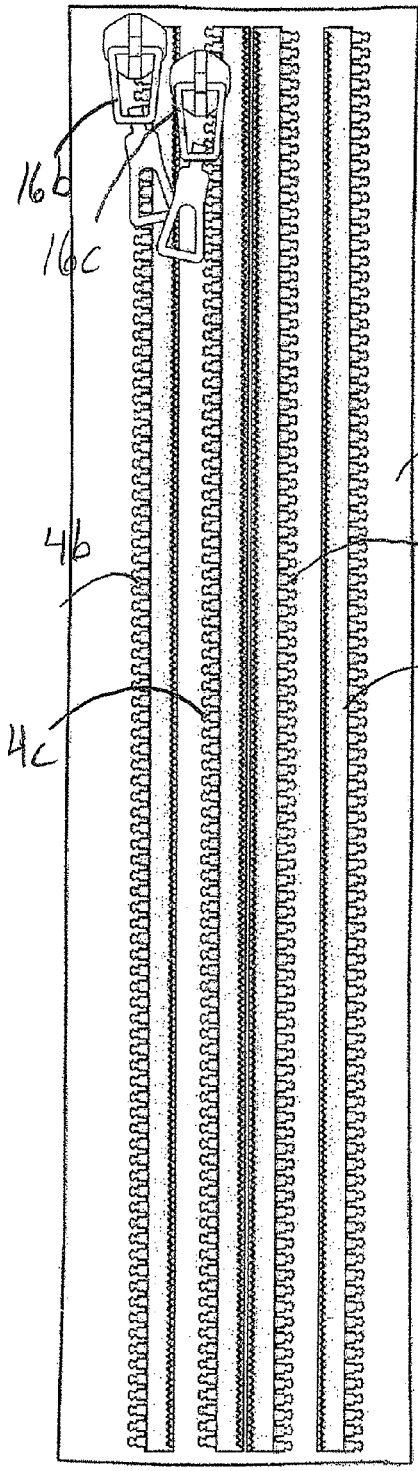
FIG. 2 is a front view of a tongue according to an embodiment of the invention.
Figure 3:
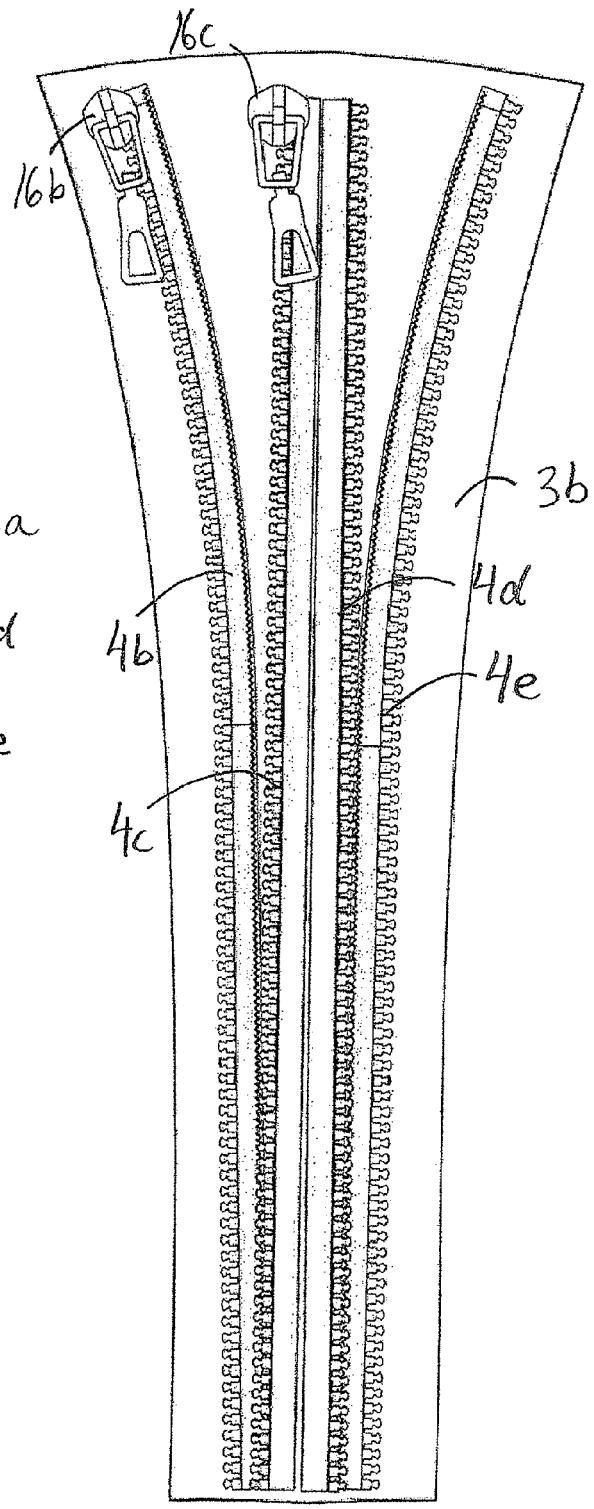
FIG. 3 is a front view of a tongue according to another embodiment of the invention.

FIGS. 2 and 3 show two examples of tongues 3a and 3b, the tongue 3a being rectangular and the tongue 3b flaring towards the top.

Figures 4, 5:
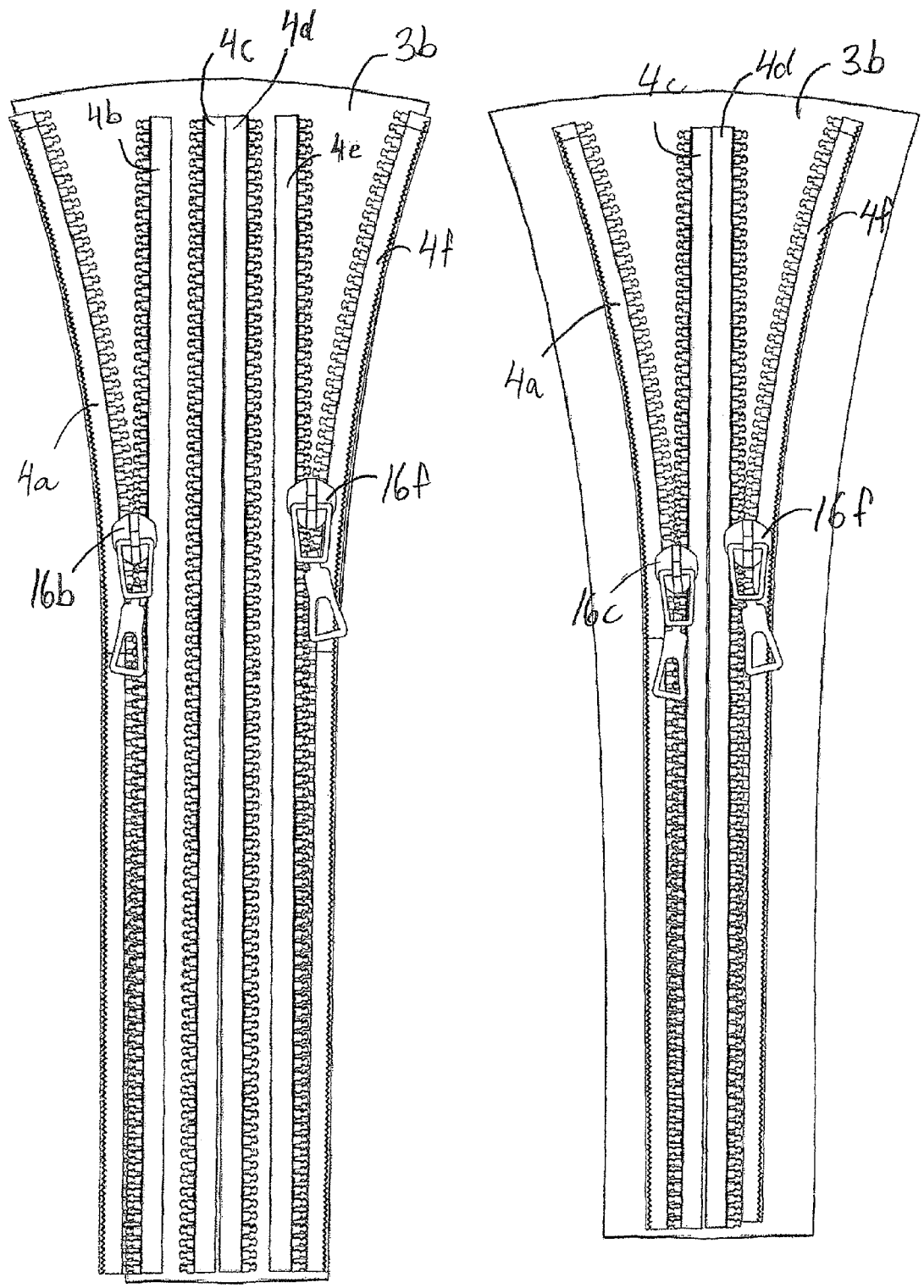
FIG. 4 is a cut-away front view of a tongue attached to a main part in a first position.
FIG. 5 is a cut-away front view of a tongue attached to a main part in a second position.

The tongues 3a, 3b are provided with a number of mating zip halves, preferably at least three, typically two pairs, but this number may be varied. Thus, an odd number of zip halves may be provided on the tongue 3, e.g. omitting zip half 4e. The left zip halves 4b and 4c are provided with zip sliders 16b and 16c for mating with a zip half 4a provided at the left edge of the main part 2 (FIG. 4). On the other side, the zip halves 4d and 4e provided on the tongues 3a, 3b are not provided with sliders since they are intended to mate a zip part 4f at the right edge of the main part 2 carrying the zip slider 16f (FIG. 4).

As best shown in FIGS. 4 and 5, the outer edges of the main part 2 are in turn provided with half of a respective zip fastener 4a and 4f. A conventional zip slider 16f is arranged at one half 4f of the zip fastener as is conventional, usually the right side seen from the front Any combination of attaching the tongue 3 to the main part 2 is possible. With two pairs of zip halves provided on the tongue 3 four combinations are possible, not counting the possibility of mating the edges of the main part 2 with the zip fasteners 4a and 4f directly with each other.

In one embodiment the distance between zip halves 4b and c is 0.5 cm, the distance between zip halves 4c and 4d is 2 cm, and the distance between zip halves 4d and 4e is 1 cm at the lower end of the legging 1. Thus, when fastening the zip halves 4a and 4f of the main part 2 with the zip halves on the tongue 3 would result in the following separation between the zip halves 4a and 4f:

attached to 4c and 4d, respectively, 2 cm, as is shown in FIG. 4, attached to 4b and 4d, respectively, 2.5 cm, (not shown)

attached to zip halves 4c and 4e, respectively, 3 cm, (not shown) and attached to zip halves 4b and 4e, respectively, 3.5 cm as is shown in FIG. 5.

Note that in the symmetrical arrangement shown in FIGS. 4 and 5, only three distances are possible.

Other embodiments may of course use other distances and a larger or smaller number of zip halves provided on the tongue 3 resulting in a wide range of possible total circumferences of the legging. The total circumference of the legging is of course the distance between the zip halves 4a and 4f when fastened to the tongue plus the whole circumference of the main part 2.

It should be noted that the separation between the zip halves on the tongue generally is not the same at the end closest to the foot as to the end closest to the knee. Generally, size variations are smaller around the lower leg than around the calf. Two persons who have the same circumference around the lower part of the leg can have quite different values around the calf. If the legging is made to fit the person with the smaller calf it will give too high pressure on the person with the bigger calf. This problem can be taken care of by different tongues.

In one embodiment of the legging 1 according to the invention, a kit of tongues 3a, 3b is provided. Each tongue has a different width and/or shape and is provided with a suitable number of zip halves (not shown). These versions can take care of small, medium and big circumferences around calf. The kit will further increase the range of possible circumferences.

An alternative fastening means is shown in FIG. 6, wherein a tongue 3' and a main part 2' are provided with fasteners 4' of hook and loop (Velcro™) type Other fastening means such as push buttons are also possible.

To receive the prescribed pressure between the legging and the leg, the material of the legging must be stretched at a certain extent to give a force corresponding to that pressure. Correct extension values can be achieved by establishing the connection between extension and force with a tensile strength tester. As the leggings shall be used for several hours the possible fatiguing properties of the materials must also be taken into account. The possible change of the mechanical properties due to washing of the leggings must also be taken into consideration.

Figure 8:
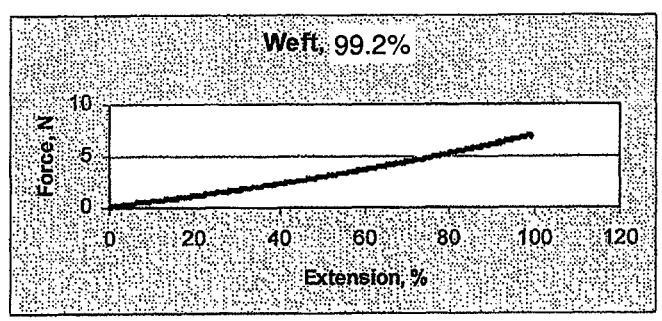
FIG. 8 is a diagram of force versus extension in percent of a material according to the invention.
Figure 9:
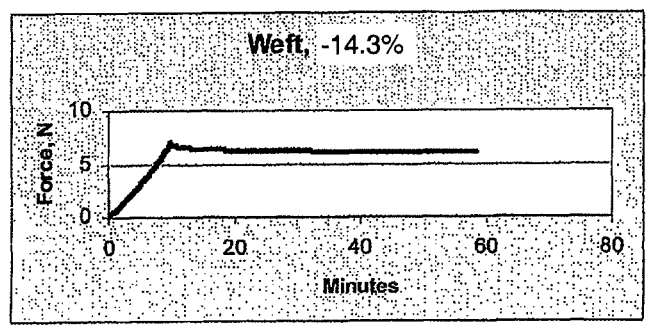
FIG. 9 is a diagram of force versus time (minutes) of a material according to the invention.

FIG. 8 shows a diagram of force versus extension in percent and FIG. 9 shows a diagram of force versus time (minutes) of a suitable material.

In one embodiment, the material is a so-called spacer fabric. A spacer fabric is principally a composite material, consisting of three material layers: a first outer layer, a second outer layer, and an intermediate layer comprising pile yarns or fibres, integrated with and interconnecting the two outer layers. A spacer fabric is manufactured in one knitted process, without the need for lamination or other adhesive means.

Woven as well as knitted spacer fabrics exists, and both weft knitted and warp knitted spacers exists. Recently, also so-called spacer fabrics based on non-woven technology have been developed.

In a suitable material, polyester yarns are knitted together with elastane, to form an elastic spacer fabric with good cushioning and stretch/recovery properties, suitable for orthopaedic end uses. This fabric is a weft knitted spacer fabric, knitted on a circular knitting machine.

The leggings may be produced in six sizes covering both women and men. As the pressure from the legging shall be highest where the lower leg has its smallest circumference this measure has been taken as the base for division in sizes. Within every single size there are "small" persons and "big" persons. If the legging is produced to give a perfect fit to persons in the centre of the size interval it is natural and unavoidable that the pressure on the "small" person will be lower than the nominal value and higher than the nominal value on the "big" person. It is therefore essential to find materials, which will give as little difference between the "big" and the "small" person as possible.

As the ratio between the minimum leg circumference and the circumference of the calf can vary widely from person to person it is necessary to divide each size in two sub sizes. Dividing the legging in two parts; the main part 2 and the tongues 3 with different sizes can take care of this.

When a flexible material is stretched to a certain level a corresponding force in the material will arise. If the material is stretched around a cylinder (corresponding to a leg) there will be a pressure between the stretched material and the cylinder. To construct leggings, which will give prescribed pressure, it is essential to know the connection between force and pressure.

When we are dealing with body limbs it will be easier to determine the circumference C (mm) instead of a cylinder diameter. Then the following formula may be used (for a flexible band with the width 50 mm).

$$F = 0.00105 P \times C.$$

F is the force (N), and P is the pressure (N/mm²=MPa)

As a practical example 20 mm Hg is selected. To achieve 20 mm Hg around the lower part of a leg with the circumference 250 mm the force (per 50 mm) should therefore be 5.24N.

The force is achieved by stretching the material. To get the needed force in a certain material we need to know the connection between extension and force for that material. Since most materials will fatigue over time we also need to know how much we must overstretch the material to get a steady state force in the material which corresponds to 20 mm Hg.

With the help of a tensile strength tester the connection between extension and force of a material can be established.

If you want a material, which is suitable for leggings that can give controlled compression with good accuracy, products with high extension should be looked for. It is also advantageous if the material is flexible in the direction around the circumference and stiff in the other, longitudinal direction, as the height of the compression device will not change substantially when the material is stretched around a body part.

When a material is stretched to a certain extension level and kept there afterwards the force in the material will decrease. The force will decline rather fast in the beginning and reach some kind of equilibrium later on, as is shown in FIG. 9. When constructing leggings with controlled compression it is necessary to compensate for this fatiguing of the material. It is positive to have a material with low fatiguing. Such a material does not have to be as much overstretched as others.

The overstretching can be painful to the patient and burdensome for the person, who shall stretch the material.

As the leggings shall be used several times and washed in between it is very positive if the mechanical properties are so little affected by wash and wear as possible. It is possible to compensate also for changes due to wash and wear but it is much more convenient if the washing restores the legging properties to a state as new.

As in all other size systems there must be "small", "medium" and "big" persons who are supposed to wear the same legging size. If the constructor has managed to fabricate a legging which gives the perfect pressure on the "medium" person it is unavoidable that the pressure on the "small" person will be lower than the nominal value and higher on the "big" person.

Let us assume that the interval around the lower leg for one of the sizes goes from 207 mm to 22 1 mm and that the prescribed pressure is 20 mm Hg. If the legging is constructed to give the prescribed pressure on a person with the circumference 2 14 mm it can be calculated (for a certain material) that the pressure on the "small" person becomes 17.8 Hg and 22.4 on the "big" one. The reason that the deviation for the "big" person is higher depends on that the slope of the 15 curve (force vs. extension) increases with the extension. To minimize the deviation the legging can be constructed for a person with a somewhat larger (214.3) circumference.

Also when the size system is constructed it can be wise to consider the possible pressure deviations within the different sizes.

If six sizes shall cover the whole range from 185 mm (circumference for small females around lower leg) to 260 mm (big males) it could be justified to divide the whole range in 6 equal ranges. This would give a range of 12.5 mm for each size. For a certain material this will give pressure deviations from 17.9 to 22.2 mm Hg within the smallest size but only 18.2 to 21.7 mm Hg within the biggest 25 size. To optimize the system the range for the bigger sizes should be made a bit larger and the smaller sizes a bit smaller. If the smallest size has a range of 11.5 mm and the biggest a range of 13.5 the pressure deviation in both ranges becomes 18.0 to 22.0 mm Hg.

The above discussion has been dealing with the possibilities of giving a defined pressure around one specific part of the leg. The legging shall however fit reasonably well on the whole lower leg and on the foot. See FIG. 7 showing a leg with reference positions. The pressure shall be rather low (<5 mm Hg) around the foot (position A to B), highest (about 17 mm Hg) around the lowest part of the leg (position C) and lower (app. 10 mm Hg) around the calf (position D). When the nominal pressure values at different body parts and the material properties are given, the garment measures at different positions (e.g. A, B, C and D) can be calculated and the garment constructed.

When we base the size system on the minimum circumference around the lower leg it is quite obvious, that two persons who have the same circumference around that part of the leg can have quite different values around the calf. If the legging is made to fit the person with the smaller calf it will give too high pressure on the person with the bigger calf. This problem can be taken care of by the tongue kit 3a, 3b, 3c discussed above with reference to FIG. 4.

The choice of legging size then has to be based on two measurements, the lowest circumference of the lower leg and the circumference of the calf.

For best function and protection the legging 1 is further inserted in an outer shell 10 suitably manufactured of hard plastic material. FIG. 10 shows an embodiment of an appliance comprising the legging inside a shell 10. The appliance 10 comprises the legging, the shell 10, an outer textile 14, an insole, an Achilles part and a sole structure 15.

While particular embodiments of the present invention have been illustrated and described for purposes of disclosure, it will be obvious to a person skilled in the art that various changes and modifications can be made with regard to material and shape etc. The scope of the invention is only limited by the claims below.

The invention claimed is:

1. A compression legging for providing compression on a body part, comprising a main part for substantially covering a main portion of the body part and a tongue, wherein
    the main part does not completely surround the body part without the tongue being attached to the main part;
    the tongue being attachable to the main part for completing the circumference around the body part;
    the main part at each edge is provided with a one half portion of a fastener attachable to the tongue;
    the main part at each edge is provided with the one half portion of the fastener, and the tongue is provided with at least three one half portions of the fastener to mate with the one half portion of the fastener provided on the main part; and
    wherein each of the one half portions of the fastener on the edge of the main part and on the tongue extend the entire lengthwise direction of the compression legging and are adapted to extend along the top of a foot of a user toward the toes of the user.

2. A compression legging according to claim 1, wherein a number of tongues having different shapes are provided, of which one tongue is to be selected for attachment to the main part.

3. A compression legging according to claim 1, wherein the fastening means comprises zip fasteners.

4. A compression legging according to claim 1, wherein the fastening means comprises hook and loop fasteners.

5. A compression legging according to claim 1, wherein the compression legging essentially is of a stretchable material.

6. A compression legging according to claim 5, wherein the stretchable material is a 3D spacer material.

7. A compression legging according to claim 5, wherein the stretchable material comprises polyester yarns knitted together with elastane.

8. A compression legging according to claim 1, wherein the compression legging further is inserted in an outer shell.

9. A compression legging according to claim 1, wherein the fastening means is openable along a full length of the compression legging.

10. A compression legging according to claim 1, wherein the legging for providing compression on a leg and foot, the main part to substantially cover sides of the leg and sides and plantar side of the foot, and the tongue being attachable to the main part for completing the circumference of lower leg and the foot.

\* \* \* \* \*